US012616960B2

(12) United States Patent
Wloka et al.

(10) Patent No.: US 12,616,960 B2
(45) Date of Patent: May 5, 2026

(54) CATALYST SYSTEM FOR PRODUCING AROMATIC AMINES

(71) Applicant: BASF SE, Ludwigshafen am Rhein (DE)

(72) Inventors: Veronika Wloka, Ludwigshafen am Rhein (DE); Dominik Garella, Ludwigshafen am Rhein (DE); Michael Reiser, Ludwigshafen am Rhein (DE); Thomas Heidemann, Ludwigshafen am Rhein (DE); Hendrik De Winne, Antwerp (BE)

(73) Assignee: BASF SE, Ludwigshafen am Rhein (DE)

( * ) Notice: Subject to any disclaimer, the term of this patent is extended or adjusted under 35 U.S.C. 154(b) by 685 days.

(21) Appl. No.: 17/602,887

(22) PCT Filed: Apr. 1, 2020

(86) PCT No.: PCT/EP2020/059228
§ 371 (c)(1),
(2) Date: Oct. 11, 2021

(87) PCT Pub. No.: WO2020/207874
PCT Pub. Date: Oct. 15, 2020

(65) Prior Publication Data
US 2022/0161237 A1 May 26, 2022

(30) Foreign Application Priority Data

Apr. 12, 2019 (EP) ...................................... 19168919

(51) Int. Cl.
| | |
|---|---|
| *B01J 23/72* | (2006.01) |
| *B01J 8/24* | (2006.01) |
| *B01J 27/224* | (2006.01) |
| *B01J 37/02* | (2006.01) |
| *B01J 37/08* | (2006.01) |
| *C07C 209/36* | (2006.01) |

(52) U.S. Cl.
CPC ................. *B01J 23/72* (2013.01); *B01J 8/24* (2013.01); *B01J 27/224* (2013.01); *B01J 37/0207* (2013.01); *B01J 37/082* (2013.01); *C07C 209/36* (2013.01)

(58) Field of Classification Search
CPC .............. C07C 206/36; C07C 564/415; C07C 564/416; C07C 564/42; C07C 564/421; C07C 564/422; C07C 564/423
See application file for complete search history.

(56) References Cited

U.S. PATENT DOCUMENTS

| | | | | | |
|---|---|---|---|---|---|
| 4,407,733 A | * | 10/1983 | Birkenstock | .......... | C07C 209/36 |
| | | | | | 502/305 |
| 5,648,312 A | * | 7/1997 | Rivas | .................... | C07C 1/0435 |
| | | | | | 502/178 |
| 5,677,257 A | * | 10/1997 | Rivas | .................... | B01J 35/633 |
| | | | | | 502/232 |

(Continued)

FOREIGN PATENT DOCUMENTS

| | | |
|---|---|---|
| CN | 1634860 A | 7/2005 |
| CN | 1657162 A | 8/2005 |

(Continued)

OTHER PUBLICATIONS

P. Klobes et al., Porosity and Specific Surface Area Measurements for Solid Materials, (2006) (Year: 2006).*
Ledoux et al., High Surface Area Silicon Carbide Doped with Zirconium for use as Heterogeneous Catalyst Support, 454 MRS Online Proceedings Library (OPL) 35-40 (1996) (Year: 1996).*
International Preliminary Report on Patentability received for PCT Patent Application No. PCT/EP2020/059228, mailed on Oct. 21, 2021, 16 pages (9 pages of English Translation and 7 pages of Original Document).
Werther, et al., "Fluidized-Bed Reactors", Ullmann's Encyclopedia of Industrial Chemistry, 2007, pp. 1-50.

(Continued)

*Primary Examiner* — Alexander R Pagano
(74) *Attorney, Agent, or Firm* — Faegre Drinker Biddle & Reath LLP

(57) ABSTRACT

The invention relates to a catalyst system suitable for hydrogenating aromatic nitro compounds (I) to form the corresponding aromatic amines (II), the catalyst system containing, as essential constituents: a component A selected from the group consisting of silicon carbide, corundum (alpha-$Al_2O_3$) and slightly porous to non-porous zirconium oxide ($ZrO_2$); and a component B, containing B1—a carrier substance selected from the group consisting of silicon dioxide, gamma-, delta- or theta-aluminum oxide $Al_2O_3$, titanium dioxide, zirconium dioxide and graphite, B2—a metal or a plurality of metals selected from the group consisting of copper, nickel, palladium, platinum and cobalt, and optionally B3—an additional metal selected from the group consisting of at least one metal selected from main group I, main group II, main group IV and sub-groups II, V, VI and VIII of the periodic table of the elements, the proportion of component A being in the range of 5 to 60 wt %, in relation to the total weight of the catalyst system, and the aromatic nitro compounds (I) being those of the general formula R—$(NO_2)_n$, (I), and the aromatic amines (II) being those of the general formula R—$(NH_2)_n$, (II), and the moieties R and indices n in formulas (I) and (II) having the following meaning: R is a substituted or unsubstituted aromatic $C_6$-$C_{10}$ moiety and n is an integer from 1 to 5.

6 Claims, No Drawings

(56) References Cited

U.S. PATENT DOCUMENTS

| 5,710,093 | A | * | 1/1998 | Rivas | B01J 35/613 |
| | | | | | 502/259 |
| 5,935,897 | A | * | 8/1999 | Trubenbach | C01B 7/04 |
| | | | | | 502/352 |
| 5,935,898 | A | * | 8/1999 | Trubenbach | B01J 37/0018 |
| | | | | | 502/232 |
| 5,952,262 | A | * | 9/1999 | Karrer | C07C 253/28 |
| | | | | | 558/328 |
| 6,140,539 | A | * | 10/2000 | Sander | C07C 209/36 |
| | | | | | 564/417 |
| 6,313,358 | B1 | * | 11/2001 | Breitscheidel | C07C 67/60 |
| | | | | | 568/864 |
| 7,256,220 | B2 | * | 8/2007 | Martinis | B01J 23/75 |
| | | | | | 518/700 |
| 7,790,937 | B2 | * | 9/2010 | Henkelmann | C07C 67/03 |
| | | | | | 568/861 |
| 7,825,062 | B2 | * | 11/2010 | Gerdes | B01J 35/60 |
| | | | | | 502/355 |
| 8,809,588 | B2 | * | 8/2014 | Konigsmann | C07C 209/36 |
| | | | | | 564/423 |
| 2005/0215800 | A1 | * | 9/2005 | Pinkos | C07D 307/20 |
| | | | | | 549/325 |
| 2007/0105713 | A1 | * | 5/2007 | Martinis | B01J 23/75 |
| | | | | | 502/259 |
| 2008/0202080 | A1 | * | 8/2008 | Barataud-Dien | F01N 3/0222 |
| | | | | | 428/116 |
| 2014/0200351 | A1 | * | 7/2014 | Bey | C07C 209/36 |
| | | | | | 546/307 |
| 2021/0379571 | A1 | * | 12/2021 | Bhasin | C07D 301/06 |

FOREIGN PATENT DOCUMENTS

| DE | 1114820 | B | 10/1961 | | |
| DE | 1133394 | B | 7/1962 | | |
| DE | 102004006104 | A | 8/2005 | | |
| EP | 1882681 | A1 | 1/2008 | | |
| FR | 2918982 | A1 | 1/2009 | | |
| GB | 0913444 | A | 12/1962 | | |
| JP | 50-104195 | A | 8/1975 | | |
| WO | 2007/025884 | A1 | 3/2007 | | |
| WO | 2008/034770 | A1 | 3/2008 | | |
| WO | WO-2009034268 | A2 | * | 3/2009 | B01J 23/50 |
| WO | 2010/130604 | A2 | 11/2010 | | |
| WO | WO-2012164231 | A1 | * | 12/2012 | B01J 23/83 |

OTHER PUBLICATIONS

International Search Report and Written Opinion received for PCT Patent Application No. PCT/EP2020/059228, mailed on Jun. 9, 2020, 12 pages.

Quiles-Diaz et al., "Catalytic performance of $CuO/Ce0.8Zr0.2O2$ loaded onto SiC-DPF in NOx-assisted combustion of diesel soot," RSC Advances, Royal Society of Chemistry, vol. 5, 2015, pp. 17018-17029.

* cited by examiner

CATALYST SYSTEM FOR PRODUCING AROMATIC AMINES

CROSS-REFERENCE TO RELATED APPLICATIONS

This application is a national stage application (under 35 U.S.C. § 371) of PCT/EP2020/059228, filed Apr. 1, 2020, which claims benefit of European Application No. 19168919.9, filed Apr. 12, 2019, both of which are incorporated herein by reference in their entirety.

The invention relates to a catalyst system and to a process for producing a catalyst system that is suitable for the production of aromatic amines (II), in particular aniline, as defined in the claims, and also to the use of the catalyst system for producing aromatic amines (II), in particular aniline, as defined in the claims, and to a process for producing aromatic amines (II), in particular aniline, using this catalyst system, as defined in the claims.

Catalysts suitable for the production of aromatic amines, for example aniline, through hydrogenation of the parent nitro compounds, and processes for the production thereof, are known.

CN-A 1 657 162 relates for example to a fluidized-bed catalyst for producing aniline through hydrogenation of nitrobenzene. The catalyst comprises silica ($SiO_2$) as support material and also copper, chromium, molybdenum, and a further metal selected from nickel, zinc, barium, vanadium, bismuth, lead or palladium. The abovementioned metals are present in the catalyst as the oxide in a specific weight ratio. Although the abovementioned metals are already introduced into the process in the form of aqueous salt solutions during production of the silica, the metals are not drawn onto the already-formed support.

A process for producing aromatic amines such as aniline through hydrogenation of the corresponding nitroaromatics with hydrogen on immobilized catalysts under adiabatic conditions is described in EP-A 1 882 681. All catalysts that can be used for the gas-phase hydrogenation of nitro compounds are in principle suitable as catalysts. The metal component of the catalysts may be present either in the form of an alloy or as a mixed oxide and the catalyst may optionally be produced using an inert support material. Examples of suitable support materials are alumina (α- and γ-modification), silica ($SiO_2$), titanium dioxide ($TiO_2$), red earth, water glass or graphite. The metals used are preferably Pd, Te, V, Nb, Ta, Cr, Mo, W, Pb or Bi. Preference is given to using α-alumina having a BET surface area of less than 10 $m^2/g$ as support material.

The reaction of aromatic nitro compounds $R$—$(NO_2)_n$ (I) with hydrogen on a catalyst usually leads to the corresponding aromatic amines $R$—$(NH_2)_n$, (II). The radicals R and the indices n are as defined below.

In addition to the fixed-bed process, a highly suitable process variant for the hydrogenation of aromatic nitro compounds, for example nitrobenzene, to aromatic amines, for example aniline, on solid catalysts is the so-called fluidized-bed process described for example in Ullmann's Encyclopedia of Industrial Chemistry vol. 15, pp. 319-366 and in particular for the production of aniline in DE 1114820 B. Here the particulate supported catalyst forms a fluidized bed.

Process requirements for such a solid catalyst, especially for a fluidized-bed catalyst, include for example good fluidity in order that a stable fluidized bed can be formed, good mechanical stability, and—for both the fixed-bed process and the fluidized-bed process—not least good thermal conductivity of the solid catalyst in order to dissipate the relatively high heat of reaction of the hydrogenation reaction from the solid catalyst to the cooling devices of the reaction vessel, for example heat exchangers.

The property profile of catalysts of the prior art suitable for the hydrogenation of aromatic nitro compounds to aromatic amines is still in need of further improvement, particularly as regards heat transfer to a cooling device, for example a heat exchanger.

The object of the present invention is to provide a catalyst system, a process for producing this catalyst system that is suitable for the production of aromatic amines (II), in particular aniline, and also the use of the catalyst system for producing aromatic amines (II), in particular aniline, and to provide a process for producing aromatic amines (II), in particular aniline, using this catalyst system.

The object is achieved by a catalyst system suitable for the hydrogenation of aromatic nitro compounds (I) to the corresponding aromatic amines (II), comprising as essential constituents a component A selected from the group consisting of silicon carbide, corundum (alpha-$Al_2O_3$) and low-porosity to non-porous zirconium oxide ($ZrO_2$) and a component B comprising B1 a support material selected from the group consisting of silica, gamma-, delta- or theta-alumina $Al_2O_3$, titanium dioxide, zirconium dioxide, and graphite and B2 one or more metals selected from the group consisting of copper, nickel, palladium, platinum, and cobalt, and optionally B3 a further metal selected from the group consisting of at least one metal selected from main group I, main group II, main group IV, and subgroups II, V, VI, and VIII of the periodic table of the elements, wherein the proportion of component A is within a range from 5% to 60% by weight based on the total weight of the catalyst system.

The object is in addition achieved by a process for producing a catalyst system as defined herein by i) producing a support material B1 comprising a component selected from the group consisting of silica, gamma-, delta- or theta-alumina $Al_2O_3$, titanium dioxide, zirconium dioxide, and graphite and contacting this support material with one or more metals B2 selected from the group consisting of copper, nickel, palladium, platinum, and cobalt, and optionally with B3 selected from the group consisting of at least one metal selected from main group I, main group II, main group IV, and subgroups II, V, VI, and VIII of the periodic table of the elements and combining this with a component A selected from the group consisting of silicon carbide, corundum (alpha-$Al_2O_3$) and low-porosity to non-porous zirconium oxide ($ZrO_2$) or ii) producing a support material B1 comprising iia) a component selected from the group consisting of silica, gamma-, delta- or theta-alumina $Al_2O_3$, titanium dioxide, zirconium dioxide, and graphite and component A selected from the group consisting of silicon carbide, corundum (alpha-$Al_2O_3$) and low-porosity to nonporous zirconium oxide ($ZrO_2$) and contacting this support material with one or more metals B2 selected from the group consisting of copper, nickel, palladium, platinum, and cobalt, and optionally with B3 selected from the group consisting of at least one metal selected from main group I, main group II, main group IV and subgroups II, V, VI, and VIII of the periodic table of the elements.

The object is also achieved by the use of the herein defined catalyst system for producing aromatic amines (II) through hydrogenation of aromatic nitro compounds (I).

Aromatic nitro compounds in the context of the present invention are those of the general formula $R$—$(NO_2)_n$ (I).

Aromatic amines in the context of the present invention are those of the general formula R—$(NH_2)_n$ (II).

In formulas (I) and (II), R and n are defined as follows:

R is a substituted or unsubstituted aromatic $C_6$ to $C_{10}$ radical, for example such unsubstituted radicals are phenyl or naphthyl, very particularly preferably phenyl. Optionally, the aromatic $C_6$ to $C_{10}$ radical, preferably the phenyl radical, may contain at least one additional substituent, for example an alkyl group such as methyl, ethyl, propyl or higher-chain alkyl substituents and/or one or more halogen substituents such as fluorine, chlorine, bromine, and iodine and/or alkyl or aryl groups substituted with heteroatoms such as N, O, S or halogen. When there are two substituents on the phenyl radical, including —$(NO_2)$ or —$(NH_2)$— groups, these substituents may be in the ortho (1,2), meta (1,3) or para (1,4) position relative to one another; when there are three substituents on the phenyl radical, including —$(NO_2)$ or —$(NH_2)$— groups, these substituents may be in the (1,2,4)-, (1,2,5)-, (1,2,6)-, (1,3,5)-, (1,3,4)- or (1,3,6)-position relative to one another.

n is an integer from 1 to 5, preferably 1 or 2.

Examples of aromatic nitro compounds (I) in the context of the present invention are mononitrobenzene (nitrobenzene), ortho-, meta- or para-dinitrobenzene, ortho-, meta- or para-mononitrotoluene, dinitrotoluene in all its isomeric forms, including by way of example those listed above for three substituents on the phenyl ring, trinitrotoluene in all its isomeric forms, preference being given to 2,4,5-trinitrotoluene and particular preference to mononitrobenzene (nitrobenzene).

The inventive catalytic hydrogenation of aromatic nitro compounds of the formula (I) leads to the corresponding aromatic amines (II), for example mononitrobenzene to monoaminobenzene, the latter also known in science and technology as aniline. The catalysts used for the hydrogenation are usually solid catalysts, for example those known in science and technology as supported catalysts, usually based on regularly or irregularly shaped particles.

Examples of aromatic amines (II) in the context of the present invention are the amines corresponding to the aromatic nitro compounds (I) mentioned above by way of example, preferably monoaminobenzene (aniline), ortho-, meta- or para-diaminobenzene, ortho-, meta- or para-monoaminotoluene, diaminotoluene in all its isomeric forms, triaminotoluene in all its isomeric forms, preference being given to 2,4,5-triaminotoluene and particular preference to aniline (monoaminobenzene).

The "catalyst system" in the context of the present invention, hereinafter also referred to as "catalyst system of the invention", is based on components A and B, the latter component comprising B1, B2, and optionally B3. These components A and/or B are generally in the form of solid particles that are usually spherical or approximately spherical in shape, but they may also be irregular. These solid particles usually have a longest diameter within a range from 20 to 1000 μm, preferably 30 to 250 μm.

The systemic character of the catalyst system of the invention is manifested by the fact that it is not necessary for the essential components A and B forming the catalyst system of the invention to be chemically and/or physically connected to one another, i.e. they may, but do not need, to be separate.

The subcomponents B1, B2, and—if present—B3 of component B are usually connected to one another; this means that these components are macroscopically physically connected, for example as particles. Such particles generally comprise the support material B1 and B2 and optionally B3 arranged therein and/or thereon, preferably evenly distributed.

It is thus for example possible for such particles to be formed from B1, B2, and optionally B3 in a layered structure, for example as core-shell particles, with the support material B1 for example forming the particle core and B2 and optionally B3 forming one or more shells arranged thereon.

It is also for example possible for such particles to be formed from B1, B2, and optionally B3 in a zonal structure, for example with B2 and optionally B3 in zones on and/or in the support material B1.

It is also for example possible for such particles to be formed from components B1, B2, and optionally B3 in structures in which these components B1, B2, and optionally B3 have undergone chemical bonding on the atomic or molecular level, for example by being present together in crystalline unit cells.

In one embodiment of the catalyst system of the invention, it is also possible for components A and B to be connected to one another, which means that these components are macroscopically physically connected, for example as particles comprising for example component B and preferably component A arranged therein and/or thereon, or as layers of a particle, for example as core-shell particles in which component A preferably forms the core and component B forms one or more shells arranged thereon, or as zones in a particle, for example component B in zones preferably on component A or else having undergone chemical bonding on the atomic or molecular level, for example by being present together in crystalline unit cells.

In a preferred embodiment, component A, thus the chemical compound constituting component A, preferably silicon carbide, is a constituent of component B1 (support material). This support material B1 or the catalyst system ii) (the latter as defined hereinbelow) may be obtained for example by the process as described below.

It is also possible for components A and B to not be connected to one another, which means that these components are not macroscopically physically connected, for example do not form layers of a particle or zones in a particle or else have not undergone chemical bonding on the atomic or molecular level. In this/these case(s), components A and B are usually present as discrete, unconnected particles A alongside B, which nevertheless for example develop their effect as a catalyst system in a defined space, for example in a reactor as a fluidized bed or as a fixed bed. This variant of the catalyst system is also referred to herein as "catalyst system i)".

It is preferable that the essential components A and B forming the catalyst system of the invention are chemically and/or physically connected to one another, with subcomponents B1, B2 and—if present—B3 of component B also chemically and/or physically connected to one another. This variant of the catalyst system is also referred to herein as "catalyst system ii)".

Further information on the catalyst system can be found in the description of the process for producing the catalyst systems of the invention.

Component A in the context of the present invention is selected from the group consisting of silicon carbide (SiC), corundum (alpha-alumina $Al_2O_3$), and low-porosity to non-porous zirconium oxide ($ZrO_2$). Component A is preferably silicon carbide (SiC).

Component A in the context of the present invention preferably has a lower BET surface area, measured using the DIN 66131 method, than component B or B1, and component A usually has little to no porosity, the porosity being measured using the DIN 66133 method. For example, the low-porosity to non-porous zirconium oxide ($ZrO_2$) in component A preferably has 50 to 95% lower porosity than the zirconium dioxide that can be used in component B1.

The proportion of component A based on the total weight of the catalyst system of the invention is within a range from 5% to 60% by weight, preferably within a range from 10% to 50% by weight, more preferably within a range from 15% to 35% by weight.

Component B in the context of the present invention comprises a support material B1 selected from the group consisting of porous silica ($SiO_2$), gamma-, delta- or theta-alumina ($Al_2O_3$), titanium dioxide, zirconium dioxide, and graphite. The support material B1 usually takes up catalytically active metals or metal compounds, as described below and as is known in supported catalyst technology. The support material B1 is usually porous and capable of being impregnated. The support material preferably comprises silica as component B1.

Component B in the context of the present invention additionally comprises B2, one or more metals selected from the group consisting of copper, nickel, palladium, platinum, and cobalt. These metals are known to those skilled in the art as active agents for the hydrogenation reaction in catalysts for aniline production.

The metals of component B2 are in the catalyst system of the invention, usually after calcining, generally present in non-elemental form, for example as an oxide or carbonate or hydroxide. These compounds are however usually reduced during the hydrogenation, that is to say in the presence of hydrogen. Preferred metals alone or in any combination in B2 are copper, nickel, and palladium, with use of copper as sole active agent B2 for the hydrogenation reaction very particularly preferred. The cumulative content of the metals in component B2, calculated in elemental form, as active agents for the hydrogenation reaction based on the total mass of the catalyst system of the invention is for copper or nickel usually within a range from 5% to 30% by weight, preferably 10% to 20% by weight, and for palladium and platinum usually within a range from 0.1% to 10% by weight, preferably 0.5% to 5% by weight.

The recited metals in component B2, for example copper, may be present in any oxidation state, for example in oxidation state +I and/or +II (e.g. for copper in the form of copper oxides); oxidation state 0 (e.g. metallic copper) is also possible.

Component B in the context of the present invention optionally comprises one or more further metals B3, also referred to herein as "dopants", as the pure element or in the form of a compound, for example as an oxide. The further metal B3 is selected from the group consisting of at least one metal selected from main group I, main group II, main group IV, and subgroups II, V, VI, and VIII of the periodic table of the elements, preferably at least one metal selected from the group consisting of potassium (K), sodium (Na), barium (Ba), lead (Pb), zinc (Zn), vanadium (V), chromium (Cr), molybdenum (Mo), tungsten (W), and iron (Fe).

The metals B3 may be present in any oxidation state, for example in oxidation state 0 as elemental metals and/or for example in oxidation states +I to +VI, for example in the form of oxides or halides or oxohalides and the like.

The metals B3 may be present in the catalyst system of the invention in any concentration, but the weight of component B3 is preferably less than the weight of component B2.

Preferred catalyst systems of the invention comprise silicon carbide as component A and a component B comprising B1 a support material, porous silica, B2 a metal, copper, and B3 selected from the group consisting of sodium, potassium, chromium, barium, and zinc, the proportion of component A being within a range from 5% to 60% by weight, preferably 10% to 50% by weight, more preferably 15% to 35% by weight, in each case based on the total weight of the catalyst system of the invention. In one embodiment of these preferred catalyst systems of the invention, component A, thus the chemical compound constituting component A, is preferably silicon carbide, a constituent of component B1 (support material) of the catalyst system of the invention.

The process for producing the catalyst system of the invention is executed such that i) a support material B1 comprising a component selected from the group consisting of silica, gamma-, delta- or theta-alumina $Al_2O_3$, titanium dioxide, zirconium dioxide and graphite, preferably silica, is produced and this support material, preferably silica, is contacted with one or more metals B2 selected from the group consisting of copper, nickel, palladium, platinum, and cobalt—usually in the form of chemical compounds thereof such as salts in complexed and/or uncomplexed form, for example carbonates, oxides, hydroxides, nitrates, nitrites, and halides such as fluoride, chloride, bromide, and iodide or the like—and optionally with B3 selected from the group consisting of at least one metal selected from main group I, main group II, main group IV and subgroups II, V, VI, and VIII of the periodic table of the elements—usually in the form of chemical compounds thereof such as salts in complexed and/or uncomplexed form, for example carbonates, oxides, hydroxides, nitrates, nitrites, and halides such as fluoride, chloride, bromide, and iodide or the like—and that this is combined with a component A selected from the group consisting of silicon carbide, corundum (alpha-$Al_2O_3$) and low-porosity to non-porous zirconium oxide ($ZrO_2$), preferably silicon carbide, hereinafter referred to as "process variant i)", which usually results in catalyst system i)
or
ii) a support material B1 comprising iia) a component selected from the group consisting of silica, gamma-, delta- or theta-alumina $Al_2O_3$, titanium dioxide, zirconium dioxide and graphite, preferably silica and iib) component A selected from the group consisting of silicon carbide, corundum (alpha-$Al_2O_3$) and low-porosity to non-porous zirconium oxide ($ZrO_2$), preferably silicon carbide, is produced and this support material is contacted with one or more metals B2 selected from the group consisting of copper, nickel, palladium, platinum, and cobalt—usually in the form of chemical compounds thereof such as salts in complexed and/or uncomplexed form, for example carbonates, oxides, hydroxides, nitrates, nitrites, and halides such as fluoride, chloride, bromide, and iodide or the like—and optionally with B3, a further metal selected from the group consisting of at least one metal selected from main group I, main group II, main group IV and subgroups II, V, VI, and VIII of the periodic table of the elements—usually in the form of chemical compounds thereof such as salts in complexed and/or uncomplexed form, for example carbonates, oxides, hydroxides, nitrates, nitrites, and halides such as fluoride, chloride, bromide, and iodide or the like, hereinafter referred to as "process variant ii)", which usually results in catalyst system ii).

Further embodiments of the process for producing the catalyst system of the invention can be subsumed under the mentioned process variants i) or ii), wherein, for all embodiments of the process for producing the catalyst system of the invention, the components A, B with B1, B2, and optionally B3 described above as preferred or exemplary may explicitly be used and are included and disclosed.

A highly suitable process for producing the catalyst system of the invention is described below by way of example.

First, the support material B1 is produced.

The support material B1 may be produced by various processes known to those skilled in the art.

A preferred process for producing the support material B1 is spray-drying, wherein in a preferred embodiment the support material B1 essentially consists of silica, and in a further preferred embodiment component A, thus the chemical compound constituting component A, preferably silicon carbide, is a constituent of support material B1.

The silica of the invention that is used is known in principle and may be produced for example as described in DE 10 2004 006 104 A or purchased as a commercial product under the name D11-20 Hydrogel (BASF SE).

In a highly suitable process, the silica of the invention is produced by the sol-gel process, which is known in principle to those skilled in the art. For example, sodium silicate, e.g. $Na_2SiO_3$, can here be reacted with acid, for example sulfuric acid. This generally gives a hydrogel (silica hydrogel) that can be treated further, for example washed with aqueous ammonia solution and/or with water containing dissolved carbon dioxide. The hydrogel material thereby obtained is usually coarse-grained and is generally then fed into a comminution process, in particular a milling process, for example in order to achieve a certain particle size.

In the context of the present invention, wet milling to a finely particulate hydrogel is particularly preferred for comminution of the hydrogel material, but the hydrogel material may also be comminuted by dry milling. It is possible to add an aqueous alkali metal hydroxide solution during or after wet milling of the hydrogel material, for example in order to increase the abrasion resistance of the finely particulate hydrogel obtained, as described in more detail in WO 2010/130604. Wet milling for example takes place in a pin mill or impact-plate mill, in particular a stirred ball mill. For spray-drying, the hydrogel material to be comminuted is usually added to a liquid. This mixture generally has a solids content of 10% to 15% by weight and a pH of 5 to 10.

The finely particulate hydrogel particles (silica hydrogel particles) obtainable during comminution, preferably wet milling, of the hydrogel material usually have an average particle diameter ($d_{50}$ value, determined by laser diffraction) within a range from 1 to 35 µm, preferably of less than 30 µm, for example 1 to 30 µm, more preferably of less than 20 µm, for example 1 to 20 µm.

The silicon carbide (SiC) of the invention is known in principle to those skilled in the art and can be obtained for example from Saint Gobain NorPro. It usually has a particle size distribution, measured by laser diffraction on a Malvern Mastersizer (ISO 13320), with an average particle diameter ($d_{50}$ value, determined by laser diffraction and calculated from the particle size distribution) of less than 100 µm. An average particle diameter of less than 30 µm, for example 1 to 30 µm, is preferred and one of less than 20 µm, for example 1 to 20 µm, particularly preferred.

A particularly suitable silicon carbide from Saint Gobain NorPro is for example SC53232, which has a determined $d_{50}$ value of 8 µm, measured by laser diffraction on a Malvern Mastersizer with measurement in water and using ultrasound.

A suspension of the finely particulate hydrogel described above, with or without addition of the above-described silicon carbide, is then usually spray-dried to obtain the support material B1. The suspending agent is for example water, organic solvents or mixtures of water and organic solvents such as lower alcohols, and is preferably water.

The method of spray-drying is known in principle to those skilled in the art. It is customary to do this in a spray tower into which the suspension to be dried (also referred to as the "slurry" or "spray slurry") is sprayed, usually with nozzles. Typical conditions for this are: Temperature in the spray tower inlet within a range from 250 to 350° C., temperature in the spray tower outlet within a range from 100 to 140° C., nozzle pressure within a range from 1.5 to 2 bar.

The preferred component B1 produced from silica during spray-drying of the finely particulate hydrogel described above preferably has a BET surface area, measured using the DIN 66131 method, of 400 to 620 m²/g.

The production, by spray-drying, of a further preferred support material B1 in which component A silicon carbide, in addition to silica, is a constituent of component B1 (support material), is described below by way of example.

A 10% to 18% by weight aqueous suspension of 80% by weight of silica (hydrogel D11-20, BASF, milled to an average particle diameter of 10 µm) and 20% by weight of silicon carbide (powder SC53232, Saint Gobain NorPro) is mixed with addition of 0.5% to 1.5% by weight of sodium hydroxide. The spray slurry thus obtainable is sprayed in a spray tower to afford a solid, pulverulent product (component B1) consisting of silicon carbide and silica. Typical conditions for this are: spray slurry temperature: 25° C., temperature in the spray tower inlet 250 to 350° C., temperature in the spray tower outlet 100 to 140° C., nozzle pressure 1.5 to 2 bar.

Support materials B1 in which component A silicon carbide, in addition to silica, is a constituent of the support material and which are preferably obtainable by the spray-drying described above are usually in particulate form and have a silica content within a range from 50% to 95% by weight, preferably within a range from 60% to 80% by weight, in each case based on the total mass of the support material B1, a silicon carbide content within a range from 5% to 50% by weight, preferably within a range from 20% to 40% by weight, in each case based on the total mass of the support material B1, a particle size distribution, measured by laser diffraction on a Malvern Mastersizer (ISO 13320), with a $d_{50}$ within a range from 50 to 160 µm, preferably within a range from 80 to 130 µm, a BET surface area, measured using the DIN 66131 method, within a range from 50 to 300 m²/g preferably within a range from 120 to 200 m²/g, an average pore volume, measured using the DIN 66133 method, within a range from 0.5 to 2 ml/g, preferably within a range from 0.6 to 1.3 ml/g.

Support materials B1 in which component A silicon carbide, in addition to silica, is a constituent of component B1 (support material) are likewise available from Saint Gobain NorPro. These powders having the designations 2016750030 and 2016750033 have a silicon carbide content of respectively 30% by weight and 50% by weight and an average particle size $d_{50}$ within a range from 80 to 150 µm, calculated from the particle size distribution determined as described above.

Another method for producing the support material B1 is co-extrusion, which is known to those skilled in the art for the production of supported catalysts and is described here by way of example for a support material B1 comprising silica and silicon carbide.

Silicon carbide, described in more detail above under spray-drying, and silica, described in more detail above under spray-drying, are kneaded in a silica:silicon carbide mixing ratio within a range from 95:5 wt.-% to 50:50 wt.-% in the presence or absence of a binder or additive, extruded into extrudates, after which the mass is dried at a temperature within a range from 80 to 150° C. and calcined in air at a temperature within a range from 400 to 750° C. The extrudates consisting of silicon carbide and silica are then milled to the desired particle size distribution.

The co-extrusion may by way of example be carried out as follows: silicon carbide powder (SC53232, Saint Gobain NorPro, $d_{50}$=8 µm, BET surface area<1 m$^2$/g) is mixed with silica D11-10 spray powder (BASF; BET surface area 480 m$^2$/g, $d_{50}$=30 µm) in a ratio of 20:70 (parts by weight) and peptized with a little dilute aqueous ammonia. Sufficient Silres MSE 100 (Wacker Chemie) is then added until the resulting composition comprises 20% by weight of silicon carbide and 80% by weight of silica. The mixture is kneaded for 30 min, a little Walocel (Dow Chemicals) is added, and sufficient water is added to produce a moldable kneading mass. After kneading for a further 30 min, the mixture is extruded into 3 mm extrudates, after which the product is dried at a temperature of 120° C. for 16 h and calcined in air at a temperature in the region of 700° C. The product produced by way of example has a BET surface area of 112 m$^2$/g and a pore volume of 0.9 ml/g. The product is then milled to the desired particle size distribution.

The particulate support material produced by way of example has a silica content within a range from 50% to 95% by weight, preferably within a range from 60% to 80% by weight, in each case based on the total mass of the support material B1, a silicon carbide content within a range from 5% to 50% by weight, preferably within a range from 20% to 40% by weight, in each case based on the total mass of the support material B1, a BET surface area within a range from 50 to 300 m$^2$/g, preferably within a range from 120 to 200 m$^2$/g, and an average pore volume within a range from 0.5 to 2 ml/g, preferably within a range from 0.6 to 1.3 ml/g. After the extrudates have been comminuted, the particulate support material has a particle size distribution with a $d_{50}$ within a range from 50 to 160 µm, preferably within a range from 80 to 130 µm.

The supporting of the components B2 and optionally B3 on the support material B1 is usually carried out by impregnating the support material B1 with the components B2 and optionally B3 using the processes known to those skilled in the art for heterogeneous catalysts.

This is preferably done by applying an aqueous solution or suspension comprising B2 one or more metals selected from the group consisting of copper, nickel, palladium, platinum, and cobalt, preferably copper and optionally at least one further metal B3 selected from the group consisting of at least one metal selected from main group I, main group II, main group IV, and subgroups II, V, VI, and VIII of the periodic table of the elements, preferably at least one metal B3 selected from the group consisting of potassium (K), sodium (Na), barium (Ba), lead (Pb), zinc (Zn), vanadium (V), chromium (Cr), molybdenum (Mo), tungsten (W), and iron (Fe), to the formed support B1, preferably comprising silica and silicon carbide, by means of the impregnation process.

Component B2, preferably copper, and the optionally further metals B3 may be added for example in the form of carbonate solutions, in particular ammoniacal carbonate solutions, or nitrate solutions. The addition may be carried out a little at a time for each metal component or else in a single step.

The component B obtained by impregnation is then dried in the usual manner and calcined in the usual manner, for example in air within a temperature range from 150 to 500° C. Impregnation, drying, and calcination processes are known to those skilled in the art.

This variant of the preferably copper-containing catalyst system of the invention preferably has a BET surface area of 50 to 200 m$^2$/g.

Component B may however also be produced by producing a support material B1 without component A, for example without silicon carbide, in analogous manner to the procedure described above. Such a component B, preferably comprising only silica as component B1, can then be present in a reaction space, for example a fixed-bed or preferably fluidized-bed reactor, together with the separate component A, preferably the silicon carbide, for example as a fluidized bed or fixed bed, thereby forming the catalyst system of the invention for the desired reaction. An example of such a reaction space is a fluidized-bed reactor and an example of such a reaction is the catalytic conversion of aromatic nitro compounds of the formula (I) into the aromatic amines of the formula (II) in the presence of hydrogen.

The preferably copper-containing catalyst system of the invention has improved heat transfer properties expressed by the k value, which is within a range from 445 to 500 W/m$^2$K, preferably within a range from 475 to 500 W/m$^2$K.

The k value is determined using the method as described in the examples and here indicates how much heat the catalyst system of the invention—in particular the embodiment of the catalyst system of the invention in which component A is a constituent of component B1—is able to transfer per heat exchanger surface and per kelvin difference in temperature. The higher the k value, the more heat the fluidized catalyst system—in particular the embodiment of the catalyst system of the invention in which component A is a constituent of component B1—is able to release, for example to a heat exchanger, or absorb.

The process for producing aromatic amines (II) through catalytic hydrogenation of the parent aromatic nitro compounds (I) is described in more detail below.

The process of the invention uses as starting materials the aromatic nitro compounds (I) corresponding to the aromatic amines (II). This means that the process of the invention replaces the nitro groups (—NO$_2$) present in the starting materials by the corresponding amino groups (—NH$_2$). In the process of the invention, it is accordingly possible to use the corresponding aromatic nitro compounds (I) containing at least one nitro substituent, with the preferred or exemplary compounds mentioned above in the definition of the aromatic nitro compounds (I) and aromatic amines (II) also explicitly included here. Particularly preferred starting materials are mononitrobenzene (nitrobenzene), nitrotoluene (such as o-, m- or p-nitrotoluene) or dinitrotoluene in all its isomeric forms. Very particular preference is given to using mononitrobenzene (nitrobenzene) as starting material in the process of the invention.

Catalytic hydrogenation in the context of the present invention means the reaction of the aromatic nitro compounds (I) with hydrogen in the presence of the catalyst system of the invention to afford the corresponding aromatic amines (II). This catalytic hydrogenation can here be carried out by methods known to those skilled in the art. For example, the pressure may be 1 to 50 bar, preferably 2 to 20 bar, more preferably 2 to 10 bar. The hydrogenation temperature is for example 150 to 400° C., preferably 200 to 300° C., more preferably 270 to 300° C.

Process variants for the reaction of the aromatic nitro compounds (I) with hydrogen in the presence of the catalyst system of the invention to afford the corresponding aromatic amines (II) are for example fluidized-bed processes or fixed-bed processes.

In a preferred embodiment, the catalyst system described above, preferably the copper-containing catalyst system, is used in a fluidized-bed reactor in the fluidized-bed process for the reaction of aromatic nitro compounds (I) with hydrogen to afford the corresponding aromatic amines (II). In this fluidized-bed process, a flow of e.g. hydrogen passes through a distributor tray in the fluidized-bed reactor from below and through the catalyst system of the invention, preferably the copper-containing catalyst system of the invention, which is generally present in the form of a fluidized bed. The aromatic nitro compound (I), preferably nitrobenzene, may for example likewise be introduced into the fluidized bed formed from the catalyst system of the invention, preferably the copper-containing catalyst system of the invention from below and/or from the side, in gaseous or preferably liquid form. Such fluidized-bed processes, for example for the catalytic hydrogenation of nitrobenzene ($C_6H_5NO_2$) to aniline ($C_6H_5NH_2$) are known in principle and are described for example in DE-B 1 114 820 and DE-B 1 133 394, the disclosure of which is explicitly incorporated herein.

In one embodiment of the fluidized-bed process for the reaction of the aromatic nitro compounds (I) with hydrogen in the presence of the catalyst system of the invention to afford the corresponding aromatic amines (II), the fluidized bed is for example provided with internals that divide the fluidized bed into a plurality of cells arranged horizontally and also a plurality of cells arranged vertically in the fluidized-bed reactor. Such fluidized-bed reactors are described for example in WO 2008/034770, the disclosure of which is explicitly incorporated herein. The cell walls of the cells are generally gas-permeable and have openings ensuring that the exchange value of the catalyst system of the invention, preferably of the copper-containing catalyst system of the invention, in the vertical direction is within a range from 1 to 100 liters/h per liter reactor volume.

In a further embodiment of the fluidized-bed process for producing aromatic amines (II) through catalytic hydrogenation of the parent aromatic nitro compounds (I) using the catalyst system of the invention, preferably the copper-containing catalyst system of the invention, the process is carried out in a fluidized-bed reactor fitted with a gas distributor. Such gas distributors are known to those skilled in the art; they are described for example in CN-A 1 634 860, the disclosure of which is explicitly incorporated herein.

The aromatic amines (II) produced in the process of the invention may optionally be subjected to one or more purification steps following the catalytic hydrogenation. For example, purification by distillation may be carried out. This allows the water present in the reaction to be removed from the aromatic amine (II) obtained from the reaction mixture by distillation, in which the water content of the aromatic amine (II) can in a single distillation step be lowered to less than 20% by weight based on the mixture of aromatic amine (II) and water. The heat of reaction evolved during the hydrogenation can be used to heat the above-described distillation. The distillation column is preferably operated at an absolute head pressure of less than 1 bar. In addition, any low boilers that arise may also be removed by distillation.

The aromatic amine (II) (crude amine (II)) obtained in the hydrogenation may optionally be extracted with an aqueous alkali metal hydroxide solution, with subsequent separation of the aqueous and organic phases. The concentration of the employed alkali metal hydroxide solution and the temperature during the extraction are set such that, in the separation of the aqueous and organic phases, the aqueous phase is the lower phase. The extraction is preferably carried out at temperatures from 30 to 50° C.

The process of the invention has the advantage that aromatic amines (II), in particular aniline, can be produced in high yield and/or high chemical purity, with the improved heat-transfer properties of the catalyst system of the invention in this highly exothermic hydrogenation reaction making it possible to achieve an increased space-time yield of aromatic amines (II).

The invention is further illustrated by the examples that follow.

EXAMPLES

Silicon carbide is also referred to as SiC. Silica is also referred to as $SiO_2$.

The parameters were determined as follows:
Particle size distribution measured by laser diffraction on a Malvern Mastersizer in accordance with ISO 13320.
Average particle diameter ($d_{50}$ value) calculated from the particle size distribution (see above).
BET surface area in accordance with DIN 66131.
Pore volume (porosity) in accordance with DIN 66133.
k Value The heat transfer in the form of the k value was measured for the catalyst system of the invention and for comparative catalysts as follows: One liter of catalyst is fluidized with nitrogen in a fluidized-bed reactor. A heating probe having a known surface area A is used to heat the fluidized catalyst to a defined temperature difference ΔT relative to the heating probe. The k value of the catalyst sample can then be determined via the electrical heating power P required.

$$k = \frac{P}{A \cdot \Delta T}$$

Abrasion

The Montecatini abrasion test simulates in a fluidized bed the mechanical load on a fluidized material, in this case the catalyst system of the invention. The abrasion apparatus consists of a nozzle plate having a nozzle diameter of 0.5 mm and with a gas- and solids-tight connection to a glass column element (diameter 30 mm). Connected to the upper part of the glass column element in a likewise gas- and solids-tight manner is a conically widening steel tube. The systems are connected to a 10 bar nitrogen supply. A pressure reducer is used to adjust the supply pressure to 6 barg for operation. The system is operated without overpressure under ambient conditions.

60.0 g of the bulk material under investigation, in this case the catalyst system of the invention, was introduced into the apparatus. The gas volume flow for the fluidization was set to 350 l/h. The high gas velocities at the nozzle result in abrasion or breakage of the particles through particle-particle and particle-wall contacts. The discharged solids pass through a pipe bend into a filter paper sleeve. The discharged material is weighed after one hour and after a further five hours in order to determine the fines content (after 1 hour) and the abrasion (after 5 hours).

Expansion

A glass fluidized-bed apparatus (QVC standard tube 500 mm in length and 50 mm in diameter) is connected to a nitrogen supply (10 bar). The apparatus was filled with 200 g of particles and gas was passed into the product by opening a ball valve in the feed line. After thorough mixing of the particles (20-30 s), the ball valve was quickly closed. Once all gas bubbles have exited the particle layer, resulting in a bubble-free fluidized bed, the bed height is immediately noted. This corresponds to the height of an expanded fluidized bed without bubbles. The bed height thereafter continues to slowly sink due to further loss of gas until an end point is reached. This corresponds to the settled bed height, which is likewise noted. The expansion is defined as the ratio of the expanded bed height to the settled bed height.

Example 1: Production of Support Material B1 from SiC and $SiO_2$

A support material consisting of silicon carbide and silica was sprayed to a solid pulverulent product by spray-drying a 13.5% by weight aqueous suspension of 80% by weight of $SiO_2$ (Hydrogel D11-20, BASF, milled to 10 μm) and 20% by weight of SiC (powder SC53232, Saint Gobain NorPro) with addition of 0.5% by weight of NaOH in a spray tower at a nozzle pressure of 1.8 bar. After sieving to remove the fines fraction, a mixed support having a BET specific surface area of 297 $m^2/g$, an Hg pore volume of 1.16 ml/g, and a $d_{50}$ value of 52 μm was obtained.

Example 2: Production of a Copper-Containing Catalyst System 150 g of the pulverulent catalyst support 2016750030 (Saint Gobain NorPro, pore volume 0.69 ml/g) consisting of silicon carbide and silica in a mass ratio of 30:70 was placed in a rotary evaporator. 50 g of an ammoniacal solution of Cu (15% by weight CuO, density d=1.244 g/l) is added to the support at 120° C. and 480 mbar. A further 240.3 g of the Cu solution is added in six further impregnation steps. After each impregnation step, the material is dried for 1 h at 120° C. and 480 mbar and in the final two impregnation steps it was dried for 2 h at 120° C. and 300 mbar. The product was forced through a 250 μm sieve in order to break up agglomerates that had formed. The catalyst was then finally heated to 390° C. in a muffle furnace at 1 K/min and calcined at 390° C. for 2 h. The catalyst system had a CuO content of 22.2% by weight and comprised particles with an average particle diameter ($d_{50}$ value) of 114 μm.

Example 3: Production of a Copper-Containing Catalyst System 3.5 kg of the pulverulent catalyst support 2016750030 (Saint Gobain NorPro, pore volume 0.69 ml/g) consisting of silicon carbide and silica in a mass ratio of 30:70 was placed in a tumble dryer and heated to 80° C. An ammoniacal solution of Cu (14% by weight CuO, density d=1.205 g/l) was sprayed on in 6 portions of 1.14 kg each (total 6.87 kg), with the material dried in the rotary tumble dryer at 80° C. for 45 min between individual impregnation steps. The spray nozzles were rinsed clean with 100 ml of 25% $NH_3$ solution. After all the impregnation solution had been added, the catalyst was dried at 80° C. for 5 h until the resulting pressure was <100 mbar. The catalyst was then finally heated to 550° C. in a muffle furnace at 1 K/min and calcined at 550° C. for 2 h. Data for the catalyst are shown in the table.

Example 4: Production of a Catalyst without SiC (Comparative)

A pulverulent $SiO_2$ support (BV0308, BASF) was impregnated with ammoniacal Cu solution, dried, and finally calcined in analogous manner to example 2. The catalyst had a CuO content of 21.2% by weight and comprised particles with an average particle diameter ($d_{50}$ value) of 112 μm.

Example 5: Production of a Further Catalyst without SiC (Comparative)

A pulverulent $SiO_2$ support (BV0308, BASF) was impregnated with ammoniacal Cu solution, dried, and finally calcined in analogous manner to example 3. Data for the catalyst are shown in the table.

Example 6: Aniline Production

The behavior of the Cu-containing catalyst system comprising an $SiC—SiO_2$ support produced in example 3 and also the behavior of a noninventive catalyst from example 5 were examined in continuous operation as follows: Preheated nitrobenzene was pumped by means of a two-phase nozzle into a 5 l fluidized-bed reactor, where it was fluidized at the nozzle opening with part of the hydrogen flow. The reaction was carried out at a temperature of 290° C., a pressure of 5 bar (6 bar absolute) with 2 $Nm^3/h$ hydrogen and 8 $Nm^3/h$ nitrogen and 1.2 kg of nitrobenzene/hour.

Using 2.2 kg of the catalyst system from example 3, a conversion of 100% and an aniline selectivity of 99.7% were achieved. The catalyst could be completely regenerated through intermediate regeneration with an air/nitrogen mixture at 220-290° C. and showed conversion of 100% and an aniline selectivity of 99.7% in the 2nd to 6th cycles too. The experiment was then ended, although the catalyst remained active. No coating with copper was observed in the deinstalled catalyst.

The results are compiled in the table below.

TABLE

| | | Aniline production | |
|---|---|---|---|
| Parameter | | Catalyst system of the invention from example 3 | Comparative catalyst system from example 5 |
| Support | | 30% SiC 70% $SiO_2$ | 100% $SiO_2$ |
| Composition $SiO_2$/SiC/CuO | % by weight | 56/24/20 | 79/0/21 |
| d50 | μm | 118 | 112 |
| Pore volume | ml/g | 0.92 | 1.18 |
| BET surface area | $m^2/g$ | 166 | 179 |
| Abrasion | % by weight | 2.3 | 8.6 |
| Density | kg/l | 2.37 | 2.18 |
| Bulk density | kg/l | 0.70 | 0.56 |
| Expansion | % | 4.3 | 4.5 |
| k value | $W/m^2K$ | 478 | 406 |
| Conversion of nitrobenzene | % | 100 | 100 |
| Selectivity for aniline | % | 99.7 | 99.7 |

The parameters listed in the table were determined as described above.

It was surprisingly found that an SiC-containing $SiO_2$ support can still be readily doped with Cu in the region of 20% by weight, even though the modification of the support means that less pore volume is available for impregnation. This was surprisingly not accompanied by an adverse effect on the conversion behavior and selectivity of the catalyst system of the invention. The catalyst system of the invention based on SiC-containing $SiO_2$ powder surprisingly achieved a disproportionately high BET surface area. The heat transfer behavior of the catalyst system of the invention (k value) is far superior to that of the comparative catalyst.

The invention claimed is:

1. A catalyst system suitable for the hydrogenation of aromatic nitro compounds (I) to the corresponding aromatic amines (II), comprising as essential constituents a component A silicon carbide, wherein component A is a constituent of component B1 and a component B comprising B1 a support material selected from the group consisting of silica, gamma-, delta- or theta-alumina $Al_2O_3$, titanium dioxide, zirconium dioxide, and graphite and B2 copper, wherein a cumulative content of the metals in component B2, calculated in elemental form, based on the total mass of the catalyst system is from 5% to 30%, and optionally B3 a further metal selected from the group consisting of at least one metal selected from main group I, main group II, main group IV, and subgroups II, V, VI, and VIII of the periodic table of the elements, wherein component A is within a range from 15% to 35% by weight based on the total weight of the catalyst system and where the aromatic nitro compounds (I) are those of the general formula R—$(NO_2)$n (I), the aromatic amines (II) are those of the general formula R—$(NO_2)$n (II), and the radicals R and indices n in formulas (I) and (II) are defined as follows: R is a substituted or unsubstituted aromatic $C_6$ to $C_{10}$ radical and n is an integer from 1 to 5 wherein the support material B1 has an average pore volume in the range from 0.6 ml/g to 1.3 ml/g, measured according to DIN 66133.

2. A process for producing a catalyst system as defined in claim 1, by i) producing a support material B1 comprising a component selected from the group consisting of silica, gamma-, delta- or theta-alumina $Al_2O_3$, titanium dioxide, zirconium dioxide, and graphite and contacting this support material with copper, and optionally with B3 selected from the group consisting of at least one metal selected from main group I, main group II, main group IV, and subgroups II, V, VI, and VIII of the periodic table of the elements, and combining this with silicon carbide.

3. A process for producing aromatic amines (II) through catalytic hydrogenation of the corresponding aromatic nitro compound (II), comprising contacting the aromatic nitro compound with the catalyst system as defined in claim 1.

4. The process according to claim 3, wherein the process is executed in the fluidized bed.

5. The process according to claim 3, wherein the aromatic amine compound (II) is aniline and the corresponding aromatic nitro compound (I) is nitrobenzene.

6. The catalyst system according to claim 1, having a k value from 445 to 500 W/m²K.

* * * * *